United States Patent [19]
Rosselli

[11] Patent Number: 6,007,519
[45] Date of Patent: Dec. 28, 1999

[54] CENTRAL ACCESS CANNULATION DEVICE

[76] Inventor: Matteo Rosselli, 128 Pine Hammock Ct., Jupiter, Fla. 33458

[21] Appl. No.: 08/903,347

[22] Filed: Jul. 30, 1997

[51] Int. Cl.$^6$ .................................................. A61M 5/178
[52] U.S. Cl. ........................................... 604/164; 604/264
[58] Field of Search .................................... 604/164, 165, 604/167, 171, 264, 280

[56] References Cited

U.S. PATENT DOCUMENTS

| | | | |
|---|---|---|---|
| 4,986,814 | 1/1991 | Burney et al. | 604/164 |
| 5,085,631 | 2/1992 | Leighton | 604/28 |
| 5,169,387 | 12/1992 | Kronner | 604/51 |
| 5,242,410 | 9/1993 | Melker | 604/164 |
| 5,295,974 | 3/1994 | O'Lauglhin | 604/198 |
| 5,667,514 | 9/1997 | Heller | 604/108 |
| 5,743,881 | 4/1998 | Demco et al. | 604/164 |

Primary Examiner—Wynn Wood Coggins
Assistant Examiner—Deborah Blyveis
Attorney, Agent, or Firm—Kevin Redmond

[57] ABSTRACT

A catheter placement system designed to permit a physician to quickly and safely place a large gage catheter into a selected major vein, while avoiding injury to the selected vein, nerves or other veins located about the area of the insertion. Initially, a small finder needle is inserted into the area where selected vein is expected to be located to cause as little damage as possible to the surrounding tissue. Once blood is drawn easily through the finder needle, the selected vein has been located. The finder needle is placed coaxially within a support tube, which is placed coaxially within the catheter. The finder needle is used as a guide for the support tube and catheter, which are moved together over the finder needle into the selected vein, with the support tube providing needed support for the usually flexible catheter to make it rigid while progressing to the selected vein. Once the catheter is placed in the selected major vein, the small needle and support tube can be withdrawn through the distal end of the catheter. During the withdrawal of the finder needle and support tube from the catheter, the finder needle is automatically locked within the support tube to prevent sticks and the rear of the catheter is automatically closed to prevent the flow of contaminated blood from the catheter and also to prevent air from entering the patients blood stream.

6 Claims, 2 Drawing Sheets

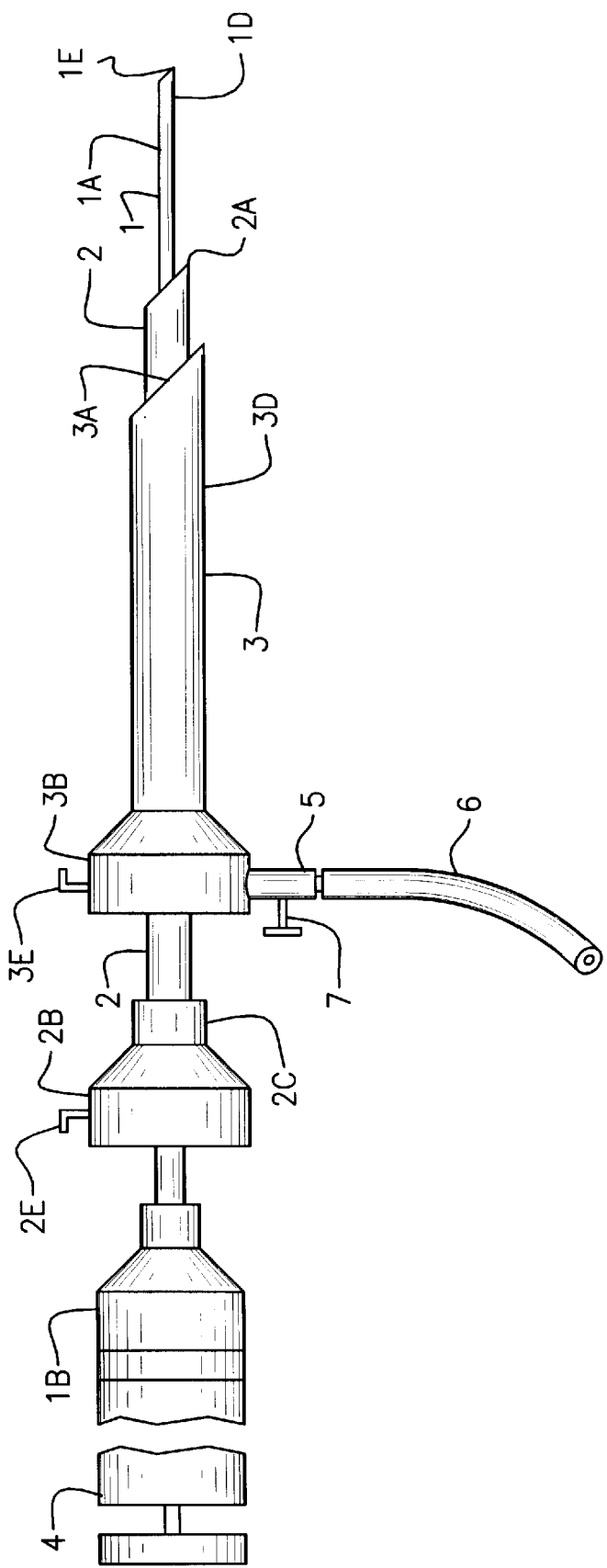
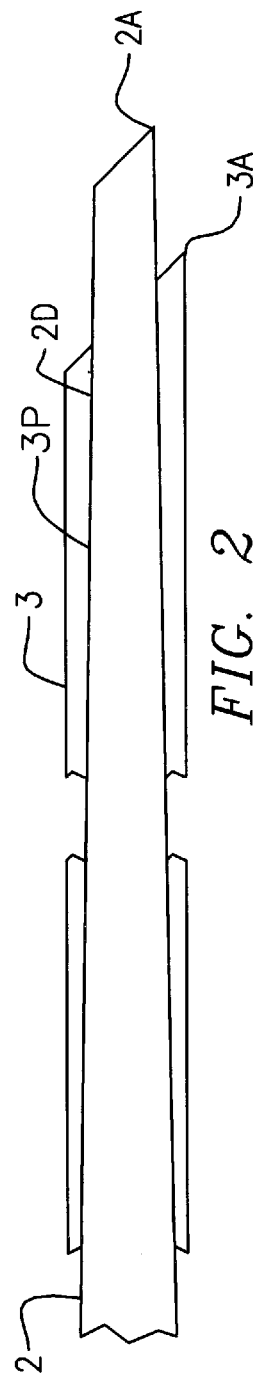

CENTRAL ACCESS CANNULATION DEVICE

PRIOR ART

In medical practices, such as anesthesiology, it is often desirable for medications to have a fast reaction time. To obtain a fast reaction time, it is usually necessary to administer large amounts of medication quickly. This is achieved by inserting such medication directly into a major artery or vein, such as the jugular, femoral or brachial vein. Smaller blood vessels are not suitable for this purpose because the medications may damage the smaller blood vessels and also the desired fast reaction time is not achieved.

It should be noted that although veins are usually used for the purpose of administering medications, arteries can also be used for this purpose and a reference to veins or blood vessels herein should be understood to also include arteries Locating a major blood vessel for the insertion of a large gage catheter has been generally carried out using the modified Seldinger technique. In this technique, a small diameter needle, as compared to say an 18 gage catheter, is inserted in the area where the selected blood vessel is expected to be located. Several insertions may be required to locate the blood vessel. The use of the small diameter needle is preferred for this procedure as it produces less damage to the surrounding area. The selected blood vessel has been located when the small diameter needle draws blood at the expected pressure for the selected blood vessel. At this point in the technique, the depth and direction of insertion of the small needle is noted and the small needle is then withdrawn. The large gage catheter is inserted in the opening made by the small needle and advanced towards the selected blood vessel with the objective of inserting the catheter into the selected blood vessel.

Unfortunately, the large catheter does not always follow the path of the small needle to the selected blood vessel and an insertion of a large catheter that misses the selected blood vessel can result in serious iatrogenic (physician caused) injury, greatly increasing the morbidity and mortality of this procedure.

Attempts have been made to overcome this problem with the modified Seldinger technique. For example, Kreuzer, et. al. in U.S. Pat. No. 5,116,323, shows an assembly which includes a catheter coaxially positioned over a guide which is coaxially positioned over a needle. The needle is inserted first to locate the selected vein. The guide tube is next advanced into the selected vein using the needle as its guide. Finally, the catheter is advanced into the selected vein using the guide to direct it to the selected vein. Once the catheter is positioned in the selected vein, the needle and the guide are withdrawn.

The problem encountered with the Kreuzer invention is the catheter, which is typically a flexible plastic tube, often does not have sufficient strength to make a wider opening than was made by the guide tube. A wider opening is necessary to provide sufficient room for the larger catheter to follow the guide tube to the vein. As a result, the catheter does not advance smoothly towards the selected vein. It can become impeded at the opening in the skin or impeded internally, causing it to expand at the point where it is impeded, and thereby making it even more difficult for the catheter to reach the selected vein. In some cases, the expansion of the catheter at the point it is impeded results in damage to the surrounding tissue.

There is a further serious problem encountered with prior art assemblies of this type. Once the catheter finally has been placed in the selected vein, the needle and the guide are withdrawn from the rear of the assembly, leaving an opening in the rear of the assembly out of which blood flows until this opening is plugged by the physician. With some patients, the blood flowing out of the rear of the assembly contains potentially lethal viruses which pose a serious threat to the physician. The sharp point of the withdrawn needle also contains the same infected blood which can result in sticking the physician, and in the physician's contracting the virus.

The problem caused by the flow of blood out of the rear of the assembly has been recognized and attempts have been made to cut off this flow. For example Yapp et al. in U.S. Pat. No. 4,735,614 discloses a valve built into the assembly which is actuated to cut off the flow by rotating a section of the assembly. Wallace in U.S. Pat. No. 5,122,120 discloses an initially resilient material which hardens with age to form a seal in the rear of the assembly to curtail the blood flow, once the needle has been withdrawn. Needles are usually dispatched to a medical waste bin and in some cases they are capped to prevent sticks while they are being handled.

All of these devices and precautions are in use in one form or another and they are helpful, in varying degrees, but they also pose several problems of their own. The initially resilient material does not always close the opening and the blood continues to leak out the rear of the assembly. The physician is often extremely busy at the time lines are being placed in the patient. Sometimes several lines must be placed quickly because the patient is in critical condition, requiring rapid surgical intervention to save his life. It is distracting to encounter difficulty in placing a line at such a time. This procedure becomes even more difficult if in addition to handling the problems with placing the lines, the physician also has to remember to stop to rotate the body of the assembly to shut off blood flow and then has to stop again to cap a withdrawn needle. Sticks with contaminated needles can and do happen at such times, with potentially fatal consequences to the physician. Methods for eliminating this and other problems encountered with prior art devices are disclosed in the following specifications and claims.

SUMMARY

An object of the present invention is to provide a catheter system which permits a physician to quickly and safely place a large gage catheter, such as an 18 gage catheter, into a selected major vein while avoiding injury to that vein as well as to nerves and other veins in the area about the point of insertion.

Another object of the present invention is to provide a method and a means for strengthening the catheter during insertion so that it can be guided to and penetrate the selected vein smoothly, and without binding, while at the same time allowing the catheter to become flexible immediately after insertion to prevent damage to the surrounding tissue.

Another object of the present invention is to automatically stop the flow of blood from the rear of the assembly once the finder needle and/or a catheter support tube have been withdrawn from the rear of the assembly, thereby providing a safety mechanism that requires no further thought or action on the part of the physician, freeing him to concentrate on other matters of critical importance.

A further objective of the present invention is to shield the tip of the finder needle automatically once it has been withdrawn from the rear of the assembly, thereby providing a second safety device that also requires no thought or action on the part of the physician at a critical time during an operation.

The present invention includes a catheter system designed to permit a physician to quickly and safely place a large gage catheter, such as an 18 gage catheter, into a selected major vein while avoiding injury to that vein as well as to nerves and other veins in the area about the point of insertion. The difficulty in inserting a large diameter catheter into such a vein is due to the uncertainty of the vein's exact location, as the location of the veins vary from individual to individual. Since more than one insertion may be necessary to locate the selected vein, it is important to do as little damage as possible with each insertion.

To accomplish this in the present invention, a small diameter needle, referred to as the finder needle, is first inserted into the area where the selected major vein is expected to be located. The finder needle produces significantly less damage than would be caused by either a larger needle or large catheter. Piercing the selected vein is indicated by the flow of blood through the finder needle back into a syringe in the catheter system. Positioned initially a distance back from the insertion end or distal end of the finder needle are the catheter and beneath the catheter a catheter support tube. The support tube surrounds a major portion of the finder needle begining at the proximal end of the finder needle. Generally the catheter, support tube and finder needle are positioned in coaxial relationship about the central longitudinal axis of the finder needle.

Once the selected vein has been penetrated by the finder needle, the catheter support tube and the large gage catheter are advanced simultaneously into the selected vein. The support tube and the catheter ride on the finder needle, using it as the guide to the vein. The finder needle and the support tube are then withdrawn from the rear of the catheter system, leaving the catheter in place within the selected vein.

During insertion of the support tube and the catheter, the support tube remain inside the catheter to provide strength to the catheter. This is a major difference between the present invention and the prior art where the soft catheter was advanced on its own. In a preferred embodiment of the present invention, the support tube has a slight rearward taper to move the catheter into the selected vein and to facilitate the support tube's removal from the catheter once the catheter has entered the selected vein. Provisions are made to automatically avoid inadvertent transmission of lethal viruses from contaminated blood during the withdrawal by automatically cutting off the flow of blood from the rear of the system and also by automatically shielding the tip of the finder needle within the support tube.

BRIEF DESCRIPTION OF THE DRAWINGS

FIG. 1 is a side view of the invention, showing it's principal components to be a catheter, a support tube, and a finder needle. All three components are coaxially located about the central axis of the finder needle with the catheter positioned over the support tube and the support tube positioned over the finder needle.

FIG. 2 is a cross sectional side view of the support tube which is positioned inside the catheter. In this embodiment, the support tube has a taper which can be seen in this Figure.

DETAILED DESCRIPTION OF THE INVENTION

Referring to FIG. 1, it can be seen that the present invention is composed of three main components, a finder needle 1, a catheter support tube 2, and a catheter 3. The catheter support tube is hereinafter referred to as simply the support tube. All three main components contain a centrally located, longitudinal hollow passageway or lumen and all three are positioned about the central longitudinal axis of the finder needle. In this position, the finder needle fits within the support tube and can be advanced through the support tube's passageway to have its tip 1E extend beyond the support tube, as can be seen to the right in FIG. 1. Similarly, the support tube fits within the catheter and can be advanced through the catheter passageway to have its tip 2A extend beyond the catheter, which also can be seen to the right in FIG. 1. The longitudinal passageway or lumen in the catheter 3 is designated by drawing numeral 3P and can be seen in the cross sectional view of the catheter shown in FIG. 2. The longitudinal passageway or lumen in the support tube 2 is designated by drawing numeral 2P and can be seen in the cross sectional view of the support tube illustrated in FIG. 3.

Figure 5:
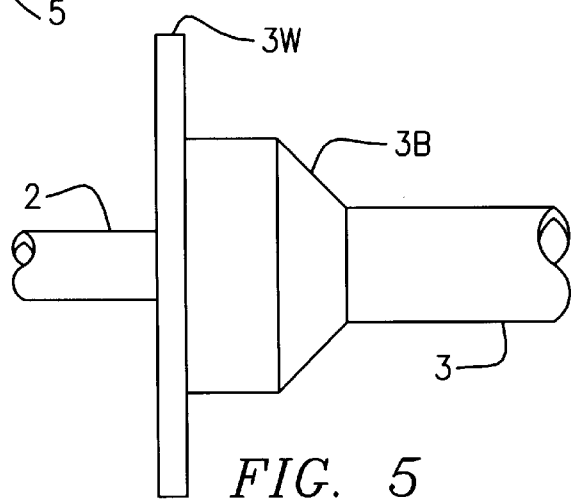
FIG. 5 is a side elevation view of the catheter hub 3B showing an embodiment which includes a winged section 3W that is attached to the hub and extends radially outwardly of the hub to provide a surface to facilitate the manipulation of the hub by a physician.

The finder needle, support tube and catheter all have their own individual hubs which are designated by drawing numbers 1B, 2B, and 3B respectively. These, hubs which can be seen to the left in FIG. 1, form the left hand termination of these three components. Attached to the left hand side of the finder needle hub 1B is a syringe 4 used to draw blood through the finder needle when a selected vein has been penetrated. In one embodiment of the present invention, wings 3W are attached at the proximal end of the hub 3B and extend radially outward of the hub as shown in FIG. 5 to facilitate manipulation of the catheter by a physician.

Extending above the support tube hub is a support hub pin 2E used for the finder needle automatic latch, which is part of a safety mechanism used to latch the finder needle within the support tube after its withdrawal from the assembly. This safety mechanism is described below in connection with the detailed description of FIG. 3. Extending above the catheter hub is a catheter hub pin 3E used to control an automatic blood flow shut off valve, which is a second safety device used to automatically shut off the flow of blood when the support tube is withdrawn from the assembly. This second safety mechanism is described below in connection with the detailed description of FIG. 4.

The finder needle and the catheter both have graduation marks, designated 1D and 3D respectively. These marks are first used to measure the depth of penetration to a selected vein by the finder needle and then used again to set the depth of penetration of the catheter to bring it to the same depth as the finder needle when the finder needle penetrated the selected vein. The use of these graduation marks helps to insure that the catheter has reached and penetrated the selected vein.

In the use of the assembly shown in FIG. 1, the finder needle 1 is advanced through the support tube 2 and the support tube is similarly advanced through the catheter until the hubs of these components are in contact. In this position, the finder needle is exposed and extends to the right well beyond the support tube, as can be seen in FIG. 1. The finder needle, which has a sharp tip 1E, is then inserted into the patient in the direction in which a selected vein is expected to be located. Once the selected vein is located, blood can be easily drawn into a syringe 4 which is connected to the left or proximal end of the finder needle as shown in FIG. 1.

The catheter with the support tube positioned firmly inside are then advanced together to the selected vein using the finder needle as a guide. The support tube has a tip 2A, which although not as sharp as that of the finder needle, is sufficient to widen the opening to the vein made by the finder needle so that the support tube and the catheter can pass through the tissue to the selected vein and then penetrate the selected vein. During the advancement of the catheter to the selected vein, the support tube, which is typically made of steel and positioned immediately beneath the catheter, stiffens the catheter by providing support, thereby preventing the otherwise flexible catheter from binding or bunching during insertion.

Once the catheter has entered the selected vein, the finder needle and the support tube are withdrawn from the rear of the assembly, leaving the catheter in the selected vein. The catheter, which is formed from a flexible plastic tube that was temporarily stiffened by the support tube during the insertion procedure, is again flexible because of the withdrawal of the support tube. This flexibility of the catheter prevents injury to the vein and the surrounding tissue because there is no longer a rigid and heavy assembly, comprising the support tube, finder needle and their hubs, extending out of the patient. The weight of this assembly, if not strapped in place, would tend to tip over and cause such injury. Even if this assembly were taped in place, it could be hit inadvertently during the placement of other lines. Withdrawal of the finder needle and the support tube avoids such problems. The catheter is typically dress over and onto the patient and then taped in place, thereby providing a low profile connection to the selected vein with little pressure on the surrounding tissue and a greatly reduced possibility of injury.

In one embodiment of the present invention, the support tube is tapered down from the proximal or left end to the distal or right end as shown in FIG. 2, with the widest diameter of the support tube being at the end 2C near the hub 2B and the smallest diameter being at the tip 2A. This configuration of the support tube prevents the catheter from sliding back over the support tube when the catheter and support tube are being advanced toward the selected vein. Before this configuration can be use with a patient, the support tube must first be advanced through the catheter under sufficient pressure to slightly expand the catheter at its hub end. This forced expansion of the catheter causes the catheter to be held with sufficient pressure about the support tube to prevent the catheter from moving relative to the support tube as the two are advanced together through the tissue to the selected vein.

Once the catheter is placed in the vein, the catheter is held at its hub end and the support tube is withdrawn. Holding the catheter hub prevents the catheter from moving back with the withdrawal of the support tube. Once the hold between the support tube and the catheter is released in this manner, the support tube can continue to be withdrawn without difficulty because the support tube taper leaves only the reduced diameter portion of the support tube in the catheter.

Referring again to FIG. 1, it can be seen that this Figure shows a rigid lateral tube 5 extending from a side of the catheter hub. Within the tube 5 is a medication control valve 3S which is actuated by an adjustment knob 7. The valve 3S is shown in the cross sectional view of FIG. 4. The knob 7 can be seen to be connected to one side of tube 5. The lateral tube is attached at one end to the catheter hub and at the other end to a flexible medication tube 6. The end of the lateral tube that is connected to the catheter hub extends inside this hub to an internal chamber 3I shown in FIG. 4. The internal chamber 3I communicates with the passageway within the catheter, permitting medications to be admitted to the selected vein by applying them through tube 6. The lateral tube also permits blood pressure monitoring to aid in determining when a selected artery has been penetrated.

Figure 3:
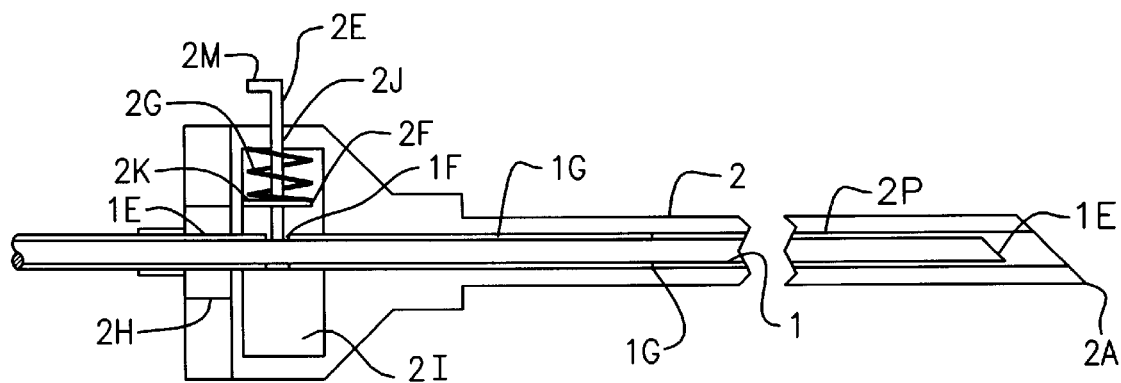
FIG. 3 is a cross sectional view of the support tube hub, illustrating a mechanism for locking the finder needle tip within the support tube before withdrawal.

FIG. 3 shows a cross sectional view of the support tube 2, and the support tube hub or simply the support hub 2B, with the finder needle 1 passing through these two components. However, the finder needle is shown in this Figure with its tip 1E withdrawn to the point where it lies totally within the passageway of the support tube and it is locked in this position by an automatic latching mechanism within the hub 2B. The purpose of this automatic latching mechanism is to prevent the finder needle tip from being exposed after being used to draw blood from a patient who is infected with a potentially lethal virus. The shielding of the tip of the finder needle in this way prevents sticks from occurring and thereby aids in preventing the transmission of this virus to the physician.

This automatic latching mechanism consists of the support hub pin 2E, a spring platform 2F, a support hub spring 2G, a sheath 1G, attached to and closely surrounding the finder needle 1, and a detent 1F in the sheath 1G. The support hub pin passes through a support hub port 2J in the top of the hub 2B and extends into and through a chamber 2I inside the hub to make contact with a side of the finder needle. The port 2J fits closely about the support hub pin 2E to prevent blood that has entered the chamber 2I from flowing outside the hub through this port.

The spring platform is a projection from a side wall of the chamber 2I that is at a point which is typically one half the distance from the finder needle to the top of the chamber 2I. This platform generally extends horizontally across the inside of the chamber 2I and loosely surround the pin 2E so as to not impede the movement of this pin. The spring 2G surrounds the pin 2E in the area between the top of the chamber 2I and the spring platform. The spring is attached at its lower end to the spring platform and at its upper end to the support hub pin 2E. The spring is biased to urge the support hub pin 2E downward against the finder needle.

The detent 1F is sufficiently wide to accept the lower end of the support hub pin 2E which locks the finder needle at a position within the support tube as shown in FIG. 3. This position prevents the tip of the finder needle 1E from being exposed and thereby reduces the risk of sticks with a contaminated needle. The support tube also has a tip 2A which must be sufficiently sharp to penetrate the patient, but this tip is not as sharp as the tip of the finder needle and it is appreciably larger, substantially reducing the risk of a stick as compared to the sticks which could easily occur with the sharp point and small diameter of the finder needle. The sheath 1G about the finder needle need not extend to the tip of the finder needle. It can be cut off at a point such as 1H shown in FIG. 3, leaving the standard, bare finder needle for insertion into the patient.

As will be apparent to those skilled in the art, the spring platform is not necessary to have a spring urge the control pin 1 against the finder needle. For example, the spring could be connected directly to the chamber wall rather than the spring platform. However, the spring platform has another purpose and that is to prevent the control pin from being urged too far down in the chamber by the spring. The support hub pin 2E contains a stop 2K which is a projection on the side of the pin that is intercepted by the spring platform. This interception prevents the pin from going past the upper side of the finder needle.

The use of the stops prevents the tip of the finder needle from being pushed into the pin and damaging the needle. To pass the finder needle through the support tube hub, it is preferable to raise the support hub pin 2E upward by grasping the pin's upper end and lifting it upward and out of the way. However, this action is not absolutely necessary in order to insert the finder needle because the pin only can penetrate downward as far at the side of the finder needle. It will ride up on the sheath 1G as the needle is inserted into the support tube. To move the finder needle beyond the detent, the control pin is lifted upward. The upper end of the pin 2E has a horizontal projection 2M which makes lifting the pin with one finger a simple task.

Figure 4:
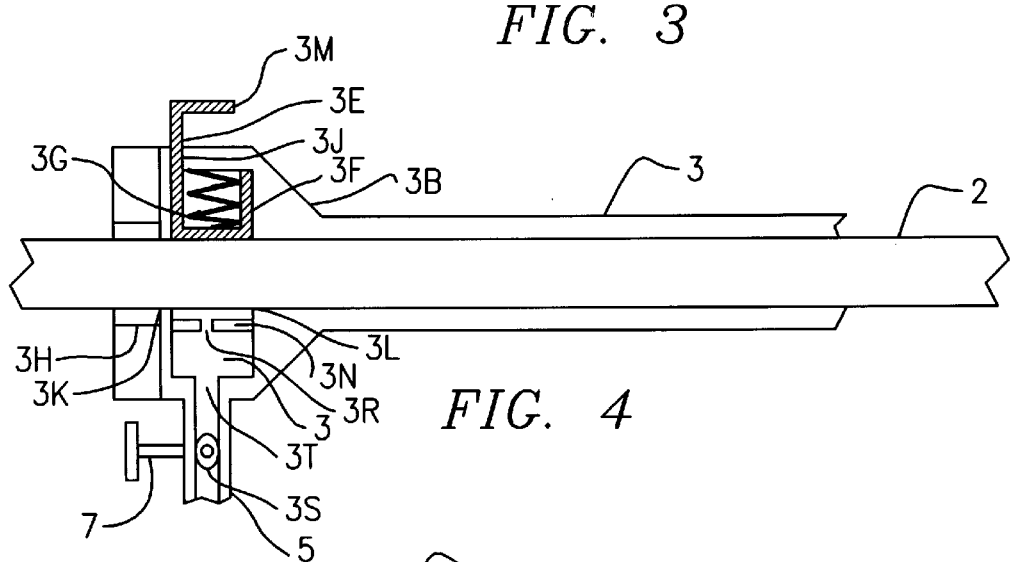
FIG. 4 is a cross sectional view of the catheter hub illustrating the mechanism for automatically cutting off the blood flow from the rear of this hub when the finder needle and the support tube are withdrawn.

The catheter hub 3B contains a second safety device which is shown in FIG. 4. This device is an automatic blood flow shut off valve, referred to hereinafter as simply the shut off valve. This device automatically prevents the flow of blood form the rear of the catheter hub when the finder needle and support tube are withdrawn. It also prevents air from entering the patients blood stream which could be catastrophic. It thereby leaves the physician free to concentrate on other matters while this device automatically does the important work of preventing the spill of contaminated blood from the catheter hub and preventing air from entering the system.

The shut off valve comprises a catheter hub pin 3E, a valve slider 3F, a catheter hub spring 3G, and a valve stop 3N. With one exception, all of these components are contained totally within a chamber 3I located within hub 3B. The exception is pin 3E which is positioned vertically and extends from the outside of the chamber at its top through a catheter hub pin port 3J in the top of the hub to the inside of the chamber at its bottom. The port 3J is sufficiently large to permit the pin 3E to move in a vertical direction, but this port also fits tightly about this pin to prevent blood within the hub from escaping to the outside.

This chamber is generally sealed from the outside except for three other ports, 3K, 3L and the port to admit lateral tube 5, 3T. During the initial phases of this procedure, lateral tube 5 is generally sealed off by valve 3S located inside tube 5, as shown in FIG. 4. Ports 3K and 3M are the left and right chamber ports respectively designed to admit the support tube and permit it to pass through the chamber into the catheter. The support tube closely fits within these ports and generally seals the chamber until it is withdrawn.

The lower end of pin 3E is connected to the valve slider 3F which, in the configuration shown in FIG. 4, is U-shaped in cross section, running parallel to the left chamber wall on the left side and parallel to the right chamber wall on the right side. The bottom element of the "U" runs horizontally and connects the left and right sides of the "U" at their bottom ends. The chamber walls are all generally vertical and provide a uniform cross section in the horizontal plane which is spanned by the valve slider. The catheter hub spring 3G is seated within the valve slider with one end resting on the bottom element of the "U" and the upper end resting against the top of the chamber. The spring 3G is biased to urge the valve slider down and against the support tube 2.

As soon as the support tube is removed, the spring continues to urge the valve slider downward past the ports 3K and 3L until it rests on the valve slider stop 3N, which is a projection from the chamber wall running generally horizontally across the chamber below these ports in the chamber. The left side of the valve slider fits closely against the left wall of the chamber 3I and when the valve slider is in its lower position resting on the slider stop, it seals the left side of the chamber completely, automatically preventing any blood flow out of the chamber. Any blood that was located immediately below the valve slider is forced down through an open in the slider stop 3R to the lower portion of the chamber. The right side of the slider contain a port 3T to allow medications entering the chamber through the lateral tube 5 to proceed through this port into the catheter and the selected vein.

The upper end of the pin 3E includes a lateral projection 3M at its top which facilitates lifting the pin and the valve slider to permit entry of the support tube on the initial set up of the assembly. Once the support tube is in place, the automatic shut off valve operates without any effort on the part of the physician, preventing unwanted, contaminated blood flow automatically upon the removal of the support tube.

It will evident to those skilled in the art that although the internal chamber of the catheter hub 3I and its associated components are drawn parallel to a vertical axis passing through the center of this chamber for illustrative purposes. It can be easily seen that virtually any axis generally orthogonal to the central axis of the catheter could be used with generally equivalent results. With further consideration, it can be seen that it is possible to use any axis whether orthogonal or not to the central axis of the catheter for this purpose and although the claims refer to the vertical axis, all axis's result in equivalent devices which are considered within the scope of the following claims.

Having described my invention, I claim:

1. A catheter placement assembly for inserting a catheter in a selected vein, comprising:
    (a) a catheter having a central longitudinal axis, a distal end, a proximal end and a lumen extending from said distal to said proximal end,
    (b) a catheter support tube having a distal end, a proximal end and a lumen extending from said distal to said proximal end, and said support tube extending coaxially through said catheter lumen,
    (d) a finder needle having a distal end, a proximal end and a lumen extending from said distal to said proximal end, said finder needle extending coaxially within and through said catheter support tube, said finder needle having a sharpened distal end extending outwardly of said distal end of said catheter support tube, said finder needle serving as a guide to a selected vein for said support tube after said sharpened distal end of said finder needle has been placed in a selected vein, and said catheter support tube having an outer surface dimension to place said support tube in contact with said catheter lumen to enable said catheter to be moved with, and be supported by said catheter support tube as said catheter support tube is guided to said selected artery by said finder needle,
    (e) a catheter hub having a proximal and a distal end, said catheter hub having its distal end attached to said proximal end of said catheter,
    (f) a catheter hub chamber defined by a hollow area within said catheter hub, said catheter hub chamber having a distal end and a proximal end and said catheter hub chamber communicating with said catheter lumen at its distal end, said catheter hub chamber including a catheter hub chamber port at its proximal end to accept said support tube and permit passage of said support tube through said catheter hub chamber into said catheter lumen, and (f) means for closing said catheter hub chamber port automatically upon the withdrawal of said support tube from said catheter hub chamber.

2. A catheter placement assembly as claimed in claim 1, wherein said catheter hub chamber contains a central vertical axis generally orthogonal to said central longitudinal axis of the catheter lumen and a uniform cross section in the horizontal plane about said vertical axis to form vertical chamber walls and wherein said means for closing said catheter hub aperture comprises:

(a) a valve slider disposed across said uniform cross section of the catheter hub chamber and extending vertically a distance greater than the vertical aperture of said chamber port, said valve slider valve being in sufficiently close, slideable contact with said chamber in the vertical direction to prevent the flow of fluid about said valve slider in the area in which said valve slider is in contact with said vertical chamber walls, said valve slider having freedom to move vertically within said catheter hub chamber to cover and uncover said catheter hub port, and (b) means for urging said valve slider downward within said catheter chamber and across said catheter hub port to automatically block the flow of blood through this port upon the removal of the support tube from said catheter hub port.

3. Apparatus as claimed in claim 2 wherein said means for urging said valve slider downward is a catheter chamber spring disposed between the catheter hub chamber and said valve slider.

4. A catheter placement assembly as claimed in claim 2, wherein said catheter hub includes a catheter hub pin port on the top of said catheter hub, and said valve slider includes a catheter hub pin attached to the top of the valve slider, said catheter hub pin extending upwards from the top of said valve slider through said catheter hub pin port to enable said valve slider to be lifted upwards manually by means of said catheter hub pin to open said catheter hub port to admit said catheter support tube into said catheter hub.

5. A catheter placement assembly as claimed in claim 1 further comprising wings which extend radially outward from the proximal end of said catheter hub to provide a means for manipulating said catheter.

6. A catheter placement assembly for inserting a catheter in a selected vein, (a) a catheter having a central longitudinal axis, a distal end, a proximal end and a lumen extending from said distal to said proximal end, (b) a catheter support tube having a distal end, a proximal end and a lumen extending from said distal to said proximal end, and said support tube extending coaxially through said catheter lumen, (d) a finder needle having a distal end, a proximal end and a lumen extending from said distal to said proximal end, said finder needle extending coaxially within and through said catheter support tube, said finder needle having a sharpened distal end extending outwardly of said distal end of said catheter support tube, said finder needle serving as a guide to a selected vein for said support tube after said sharpened distal end of said finder needle has been placed in a selected vein, and said catheter support tube having an outer surface dimension to place said support tube in contact with said catheter lumen to enable said catheter to be moved with, and be supported by said catheter support tube as said catheter support tube is guided to said selected artery by said finder needle, (e) a support tube hub having a proximal and a distal end, the distal end of said support tube hub being connected to the proximal end of said support tube, said support tube hub containing an internal chamber which communicates with said support tube lumen, said support tube hub further containing a support tube pin port at its top, and a support tube hub port at its proximal end, said support tube hub port communicating with the internal chamber of said support tube hub to admit said finder needle to said internal chamber and to said lumen of said support tube, (f) a plastic sheath about said finder needle, said sheath having a detent, (g) a support tube pin having an upper and lower end and being positioned vertically within said internal chamber to engage said detent in said sheath at its lower end, and said support tube pin at its upper end extending upwards through said support tube pin port to enable said support tube pin to be lifted manually and release said finder needle when desired for proper disposal after withdrawal from said selected vein, and (h) resilient means to urge said support tube pin downward into said detent to lock said finder needle within said support tube to prevent sticks with said finder needle.

* * * * *